United States Patent
Anderson et al.

(10) Patent No.: US 6,745,071 B1
(45) Date of Patent: Jun. 1, 2004

(54) IONTOPHORETIC DRUG DELIVERY SYSTEM

(75) Inventors: Carter R. Anderson, Inver Grove Heights, MN (US); Russell L. Morris, Lindstrom, MN (US); Clayton J. Anderson, Burnsville, MN (US); Lori A. Grace, Lino Lakes, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 0 days.

(21) Appl. No.: 10/371,851

(22) Filed: Feb. 21, 2003

(51) Int. Cl.[7] .................................................. A61N 1/30
(52) U.S. Cl. ........................................ 604/20; 607/149
(58) Field of Search .......................... 604/20, 115, 501; 607/153, 148, 149, 151, 152

(56) References Cited

U.S. PATENT DOCUMENTS

| | | | |
|---|---|---|---|
| 5,087,241 A | | 2/1992 | Mathiesen et al. |
| 5,087,242 A | | 2/1992 | Petelenz et al. |
| 5,158,537 A | | 10/1992 | Haak et al. |
| 5,254,081 A | | 10/1993 | Maurer et al. |
| 5,288,289 A | | 2/1994 | Haak et al. |
| 5,310,404 A | | 5/1994 | Gyory et al. |
| 5,320,598 A | | 6/1994 | Haak et al. |
| 5,358,483 A | | 10/1994 | Sibalis |
| 5,385,543 A | | 1/1995 | Haak et al. |
| 5,387,189 A | * | 2/1995 | Gory et al. .................... 604/20 |
| 5,431,625 A | | 7/1995 | Fabian et al. |
| 5,445,609 A | * | 8/1995 | Lattin et al. ................... 604/20 |
| 5,458,569 A | | 10/1995 | Kirk, III et al. |
| 5,466,217 A | | 11/1995 | Myers et al. |
| 5,605,536 A | | 2/1997 | Sibalis |
| 5,645,526 A | * | 7/1997 | Flower ......................... 604/20 |
| 5,645,527 A | | 7/1997 | Beck |
| 5,651,768 A | | 7/1997 | Sibalis |
| 5,685,837 A | | 11/1997 | Horstmann |
| 5,730,716 A | | 3/1998 | Beck et al. |
| 5,738,647 A | | 4/1998 | Bernhard et al. |
| 5,817,044 A | | 10/1998 | Evers et al. |
| 5,830,175 A | * | 11/1998 | Flower ......................... 604/20 |
| 5,846,217 A | | 12/1998 | Beck et al. |
| 6,148,232 A | * | 11/2000 | Avrahami ..................... 604/20 |
| 6,223,075 B1 | | 4/2001 | Beck et al. |
| 6,421,561 B1 | | 7/2002 | Morris |
| 6,496,727 B1 | | 12/2002 | Bernhard et al. |
| 6,510,341 B1 | * | 1/2003 | Kuribayashi et al. ......... 604/20 |
| 6,587,717 B1 | * | 7/2003 | Kuribayashi et al. ......... 604/20 |
| 6,654,635 B1 | * | 11/2003 | Koga et al. ................... 604/20 |

OTHER PUBLICATIONS

International Search Report.

* cited by examiner

Primary Examiner—Brian L. Casler
Assistant Examiner—Cris L. Rodriguez
(74) Attorney, Agent, or Firm—Nikolai & Mersereau, P.A.; C. G. Mersereau

(57) ABSTRACT

A reliable, self-contained iontophoretic drug delivery system is disclosed which enjoys a long stable shelf life and which is easy for the user to activate and employ. This system includes a wearable iontophoretic device that is prepackaged as a complete self-contained unit which includes the active species or drug to be administered and counter ions. The system includes a provision for isolating moisture sources from the electrodes and from the power source during storage and provides a simple, user-friendly mechanism to connect the drug to be administered and counter ion reservoirs to the electrodes and the device to the skin of a user in order to activate the device circuit. All elements of the device are contained in a single outer package.

17 Claims, 8 Drawing Sheets

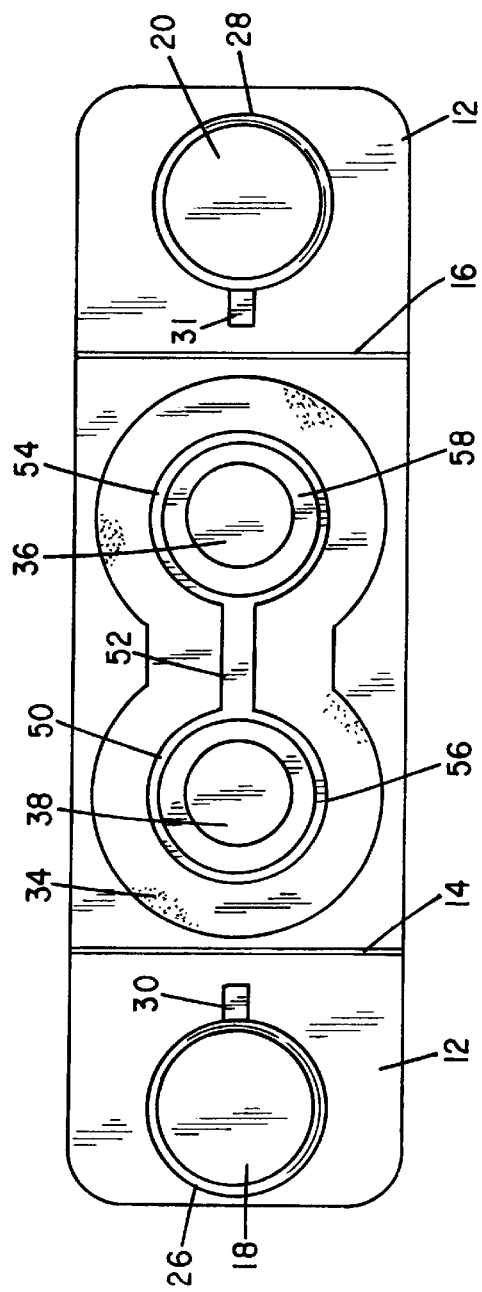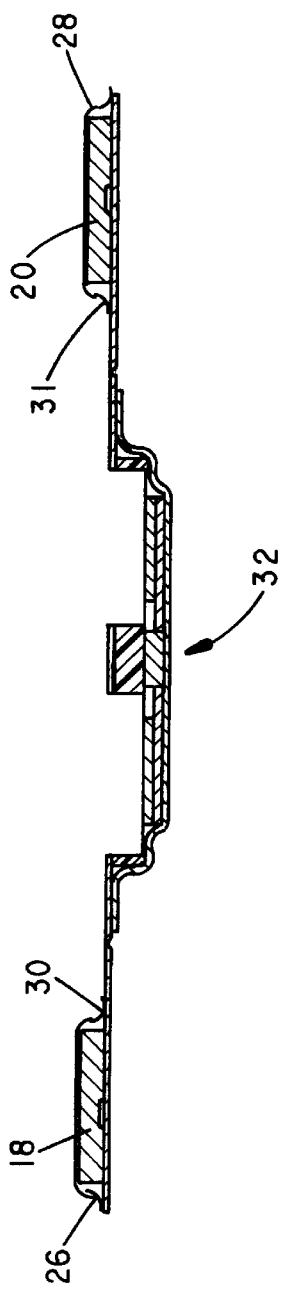

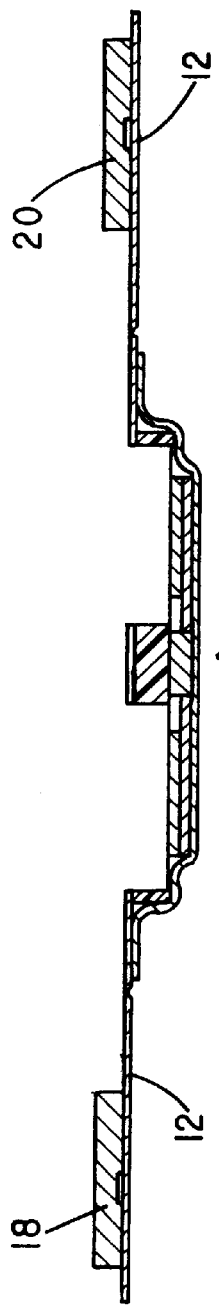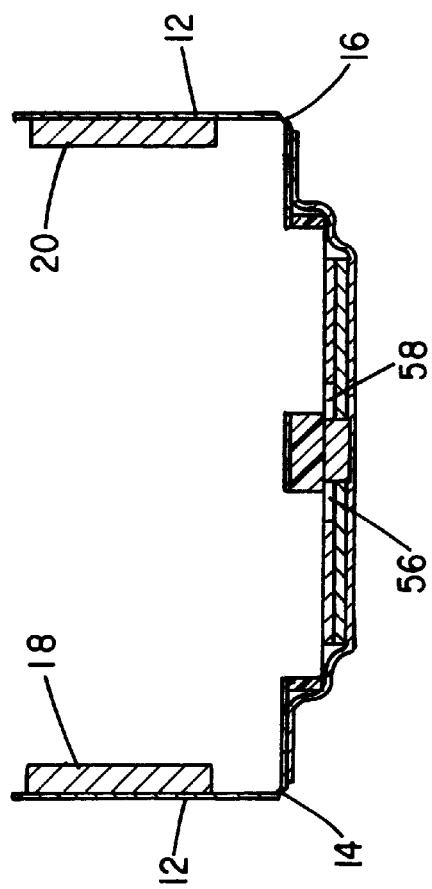

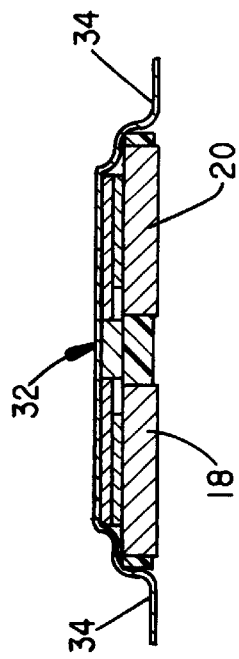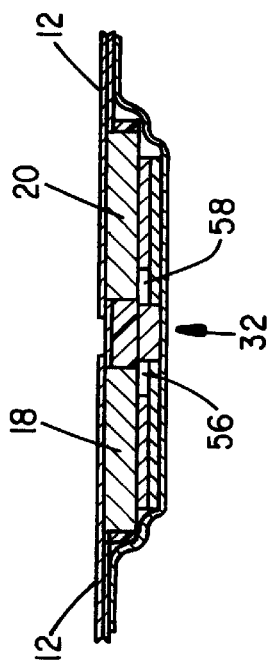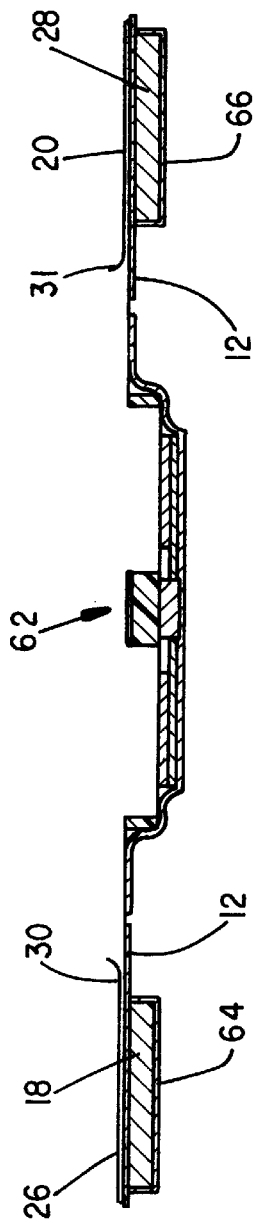

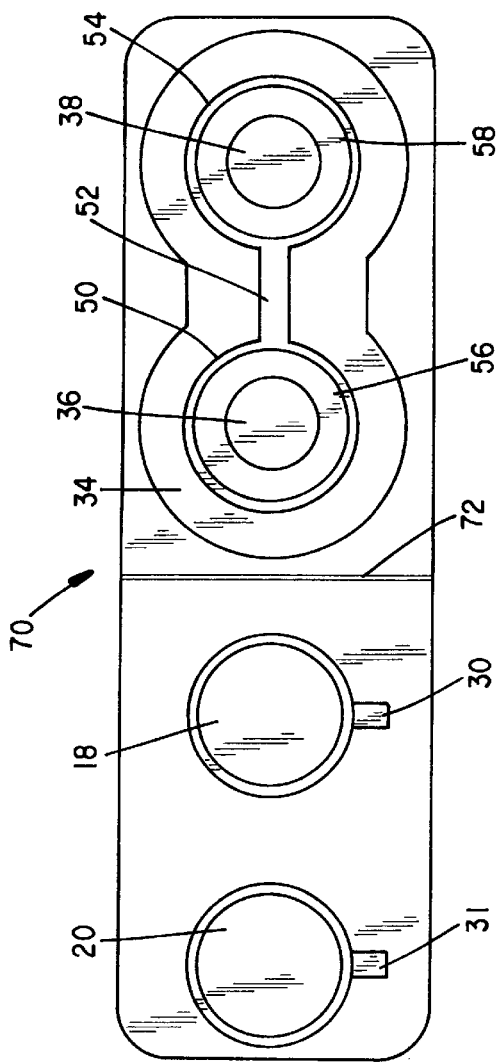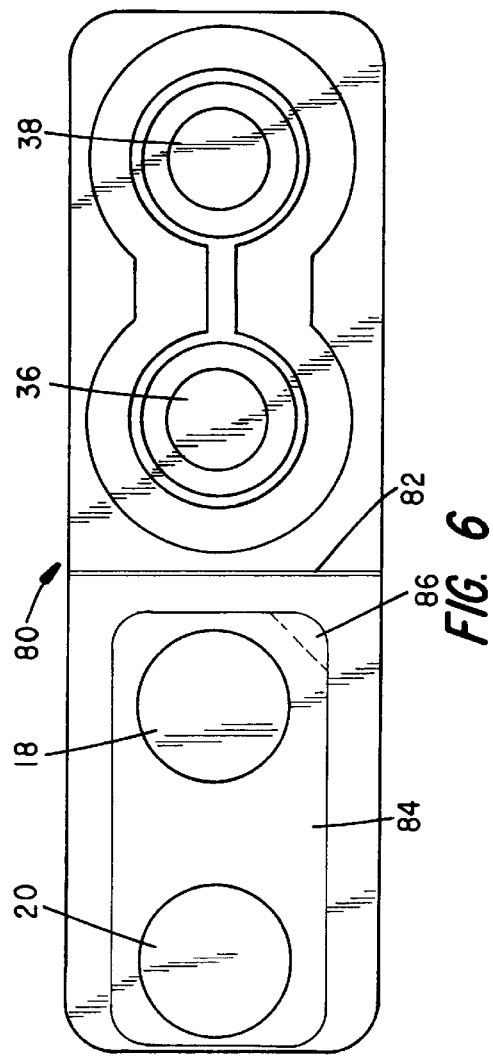

IONTOPHORETIC DRUG DELIVERY SYSTEM

BACKGROUND OF THE INVENTION

I. Field of the Invention

The present invention concerns transdermal delivery of therapeutic agents by the use of skin worn devices. More particularly, the invention is directed to a system that is wearable and utilizes the principle of iontophoresis as a means of introducing substances into the body. The system is packaged as a self-contained easily activated system in the form of a rather small skin worn patch that contains electrodes and a therapeutic agent. When applied to the skin, the system completes a circuit and can initiate a flow and controlled duration of current corresponding to the desired rate and amount of therapeutic agent to be delivered.

II. Related Art

The process of iontophoresis was described by LeDuc in 1908, and has since found commercial use in the delivery of ionically charged compounds such as pilocarpine, dexamethasone, and lidocaine. In this delivery method, ions bearing a positive charge are driven across the skin at the site of an electrolytic electrical system anode, while ions bearing a negative charge are driven across the skin at the site of an electrolytic electrical system cathode.

With iontophoretic devices, the application time and level of current flow (usually reported in units of milli-amp minutes) between the anode and cathode is directly correlated to the amount of drug delivered. The efficiency of drug delivery in an iontophoretic system can be measured by the proportion of current carried by drug molecules, relative to the current carried by competing non-medication ions having the same charge as the medication.

Iontophoresis devices conventionally have included two electrodes attached to a patient, each connected via a wire to a microprocessor controlled electrical instrument. Medication is placed under one or both of the electrodes, for delivery into the body as the instrument is activated. The instrument is designed to regulate current flow and application time. Examples of such instruments are described in U.S. Pat. Nos. 5,254,081, and 5,431,625. Power for these devices is usually provided by DC batteries, which when providing power for the microprocessor controlled circuitry allow application of a voltage to the electrodes to create a regulated current flow. These microprocessor systems are disadvantaged by the fact that patients are 'attached by wire' to an instrument, which limits patient mobility and ability to conduct normal daily activities. A typical application period for creation of skin anesthesia is approximately 10–20 minutes, which consumes instrument, caregiver, and patient time.

More recently, wearable iontophoretic systems have been developed in which the electrical circuitry and power supplied are integrated into a single patch. These systems are advantageous in that they do not have external wires, and they are much smaller in size. Examples of such systems can be found in U.S. Pat. Nos. 5,358,483; 5,458,569; 5,466,217; 5,605,536; and 5,651,768.

Typically, drug ions are delivered into the body from an aqueous 'drug' reservoir contained in the iontophoretic device, and counter ions of opposite charge are delivered from a 'counter' reservoir. A critical step in iontophoresis involves the process for incorporation of drug ions and counter ions into the device. It is well know that if such a device is improperly loaded, the device will not perform as desired.

Most often, drug/ion solutions are stored remotely in bulk quantity and introduced to an absorbent layer of the iontophoresis electrode at the time of use. Examples of such systems are described in U.S. Pat. Nos. 5,087,241; 5,087,242; 5,846,217; and 6,421,561. An advantage to this approach is that the electrodes are packaged and stored in a dry state, which is optimal for shelf life. A disadvantage to this approach is that the electrodes can be easily over-filled or under-filled, thus this aspect requires trained personnel with good technique. Additionally, because the drug solution is stored separately from the electrodes, management of two inventories is required.

To avoid the need for users to incorporate the aqueous drug or ion reservoir at the time of use, the drug solution can be pre-packaged into the electrode. Unfortunately, this inevitably reduces shelf life. During storage, moisture emanating from the drug solution can be absorbed into adjacent materials, resulting in corrosion of metallic components, degradation of power sources, and inadequate hydration of the drug pad. U.S. Pat. Nos. 5,738,647 and 5,817,044 discloses a device where an aqueous reservoir is stored in contact with an electrode assembly, and a dry medicament layer introduced to the aqueous reservoir at the time of use. Unfortunately, with this configuration the electrode is still stored in wet environment, and is therefore susceptible to corrosive deterioration.

In U.S. Pat. No. 5,685,837, a system is described in which a drug of interest, in a dry form, is pre-packaged into the electrode(s). This offers two advantages. First, moisture is not present to compromise the integrity of metallic electrode components during storage, and second, the drug of interest remains very stable. This offers a particular advantage for the delivery of certain drugs, such as large polypeptides, which have a poor stability in solution form. However, this approach requires a moisture activation step at the time of use, which can involve a time delay or introduce a reason for mechanistic failure.

Many patents describe systems where drug solutions are co-packaged with the iontophoretic device, but positioned apart from the electrodes and other metallic components until an 'activation' step is implemented at the time of use. U.S. Pat. Nos. 5,158,537; 5,288,289; 5,310,404; 5,320,598; 5,385,543; 5,645,527; 5,730,716; and 6,223,075 describe such devices. In these devices, a co-packaged electrolyte constituent liquid is stored remotely from the electrodes, in a rupturable container and a mechanical action step at the time of use induces a fluid transfer to a receiving reservoir adjacent to the electrodes. These systems enable precise fluid volumes to be incorporated at the time of manufacture to avoid overfilling; however, these devices are mechanically complex, and can fail if, for example, the package is squeezed during shipping, the container breaks and fluids are pre-maturely released. Other failure modes include compromising of the fluid delivery path during storage, if for example, outgassing hydrophobic plasticizer material is absorbed into the fluid channel, inhibiting the transfer of fluid at the time of use.

Another strategy to incorporate drug into the iontophoretic device is described in U.S. Pat. No. 4,383,529. In that disclosure, a preformed gel containing the drug is transferred into an electrode receptacle at the time of use. The advantages of this system include the provision of a precise pre-determined volume of drug gel to prevent overfilling, and the fact that using the gel form of the drug matrix insures that liquid will not 'leak' during storage or transfer. A significant disadvantage to the device described, however, exists because the user is required to visually align the gel into the receptacle at the time of use, which is a process that may be difficult for elderly patients. Additionally, that device requires the user to apply a mucilage material to the electrode prior to incorporating the gel so as to insure the integrity of the electrical contact between the electrode and the drug gel. Furthermore, it is necessary at the time of use to rotate the gel over the mucilage layer to remove entrapped air, which introduces another technique-dependant source of error. Finally, the gels of interest are stored separately from the electrodes in a plastic bag, or the like, and this requires management and storage of two separate components.

Thus, while there exists a variety of devices in the class, each of which has certain attributes, there remains a need for a single iontophoretic drug delivery system that combines the desired attributes and eliminates the drawbacks recited above. The present invention provides such a device in the form of an iontophoretic drug delivery system that is reliable, self-contained, simple to use, and shelf-stable.

SUMMARY OF THE INVENTION

The present invention solves many of the problems associated with prior self-contained iontophoretic drug delivery systems by the provision of a reliable, selfcontained system which enjoys a long stable shelf life and which is also quite easy to use. The present invention contemplates a wearable iontophoretic device that is prepackaged as a complete self-contained unit which includes the active species or drug to be administered and counter ions. The system includes a provision for isolating moisture sources from the electrodes and from the power source during storage to optimize shelf stability. The inventive system provides a simple, user-friendly mechanism to transfer the drug to be administered and counter ion reservoirs to the electrodes in order to activate the device circuit. The self-contained iontophoretic drug delivery system of the present invention contemplates the storage of all elements of the device in a single device to be activated in a single outer package. Depending on the drug or other therapeutic active species to be administered, the particular ion species may be selectively or optionally stored in either a dry state or a wet state in order to optimize shelf stability.

It is an important aspect of the present invention that it provides a complete, self-contained packaged device that includes all of the components necessary for iontophoretic delivery, including a wearable device; an aqueous anodic matrix; and an aqueous cathodic matrix. All three components (as stored) are carried on a thin, planar substrate, which additionally serves as a release liner, that is removed during device activation. No external components need to be included. If the active species or drug to be delivered is of a positive charge, it is associated with the anodic electrode, if the drug to be delivered is of a negative charge, it is associated with the cathodic electrode.

The entire device including the substrate and its components are packaged together, preferably in a conventional medical foil storage pouch or the like (not shown in figures). Within the foil pouch, the cathodic and anodic aqueous matrixes are each isolated from the iontophoretic device by a water impermeable release membrane which is peeled away and removed at the time of activation. In the event that the drug to be delivered remains stable when dissolved in an aqueous solution, the drug is incorporated into the appropriate aqueous matrix at the time of manufacture. If, however, the drug has a limited shelf stability when dissolved, the drug is incorporated as a dry layer adjacent the related electrode of the iontophoretic device, and dissolved into the aqueous matrix at the time of activation.

The activation and placement of the device is rapid and simple. First, the sealed storage pouch is breached revealing the substrate and its three components with the cathodic and anodic aqueous matrices remaining isolated from the iontophoretic device separated by the water impermeable membranes indicated above. To activate the device, water impermeable membrane covers which isolate the cathodic and anodic aqueous matrices are simply peeled away and removed. The substrate is then folded inward on itself at predetermined locations to engage the aqueous matrices with the iontophoretic device. For this purpose, one or more clearly visible fold lines are preferably provided on the substrate to insure proper alignment as the device is folded. An adhesive material provided on the iontophoretic device serves to secure the aqueous matrices to the device as they are engaged during the folding step. Engagement of the aqueous matrices, activates the device and the then activated device can be removed from the substrate or release liner ply and be placed on the body to begin drug delivery.

A key element to this invention is the ease of successful transfer of the anodic and cathodic aqueous matrices to the iontophoretic device at the time of activation which is facilitated by the incorporation of fold lines (which may be score lines, perforations or the like) that insure proper folded alignment. Additionally, the matrices need to be kept in place during the act of folding the substrate. While this can be accomplished in various ways, preferably a minor amount of releasing packaging adhesive material is provided to hold the matrices in place. Alternatively, they may be held in place without adhesives by containment in a recessed portion provided in the substrate. Successful transfer of the matrix to the iontophoretic device requires that an adhesive present on the surface of the receiving device (transfer adhesive) form a bond that is stronger than that of the packaging adhesive material that fixed the matrices to the release liner or substrate. It has also been found that the adhesive material on the iontophoretic device should ideally surround at least a portion of the electrode, so as to maintain adequate contact between the electrode and matrix during the iontophoresis process.

BRIEF DESCRIPTION OF THE DRAWINGS

In the drawings wherein like numerals depict like parts throughout the same:

FIG. 2 is a top view of the embodiment of FIGS. 1a and 1b;

FIGS. 3a–3e are schematic cross sectional views of the device of FIG. 1, during stepwise activation for use;

FIG. 4 is a schematic cross sectional view of an alternate embodiment of the device of the invention;

FIG. 5 is a top view of another embodiment of the device of the invention;

FIG. 6 is a top view of an alternate configuration of the device of FIG. 5;

DETAILED DESCRIPTION

The present invention provides a fully self-contained easy-to-use iontophoresis system in a single pre-packaged unit. Nothing needs to be added to the pre-packaged unit for activation and use. Except for the removal of release liners or backing layers and one or more simple folding operations, the device is completely ready to use. Several possible preferred embodiments of devices encompassing the inventive concepts will next be described. These embodiments are presented to illustrate the concepts of the invention and they are not meant to be construed as limiting in any manner.

Figure 1A:
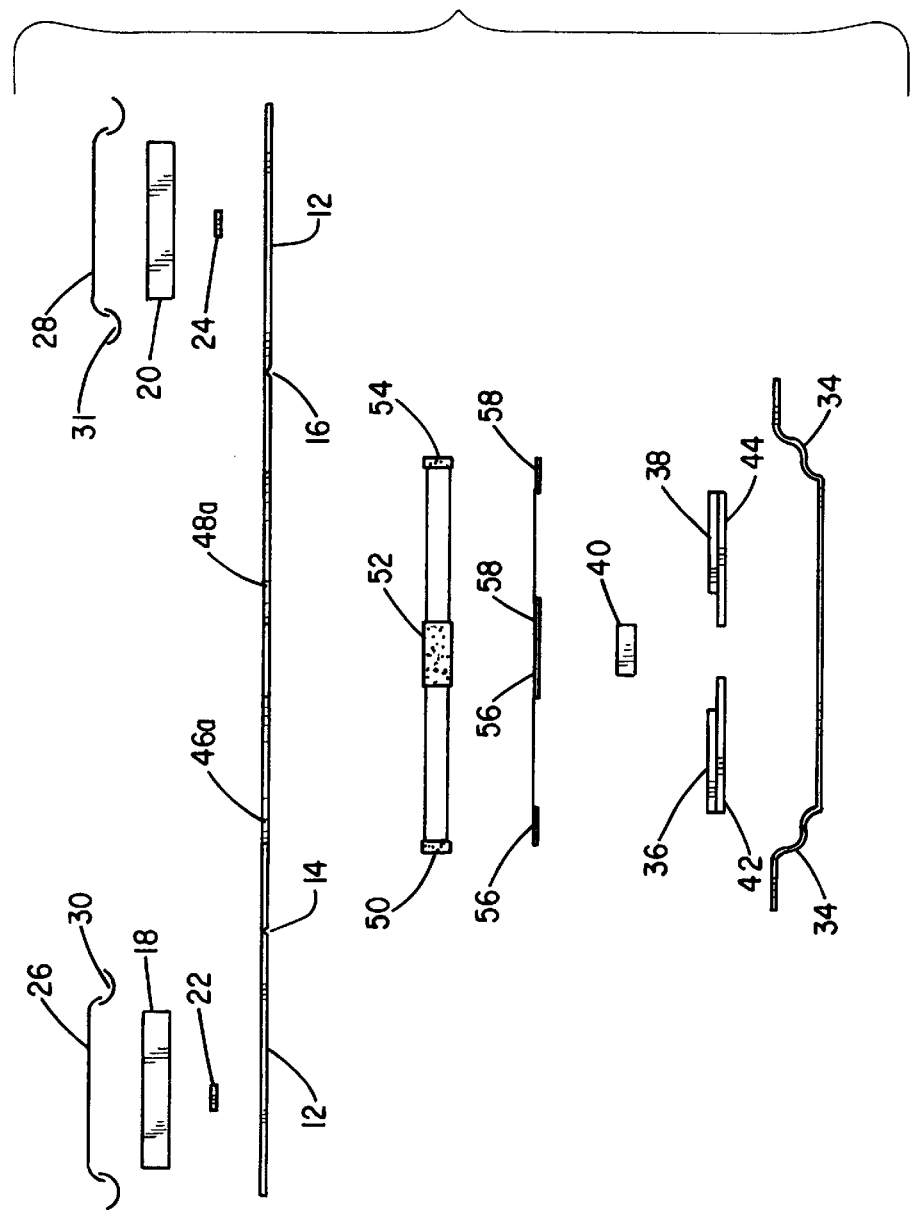
FIG. 1a is an exploded schematic view of one embodiment of a device constructed in accordance with the invention as it is packaged and stored.
Figure 1B:
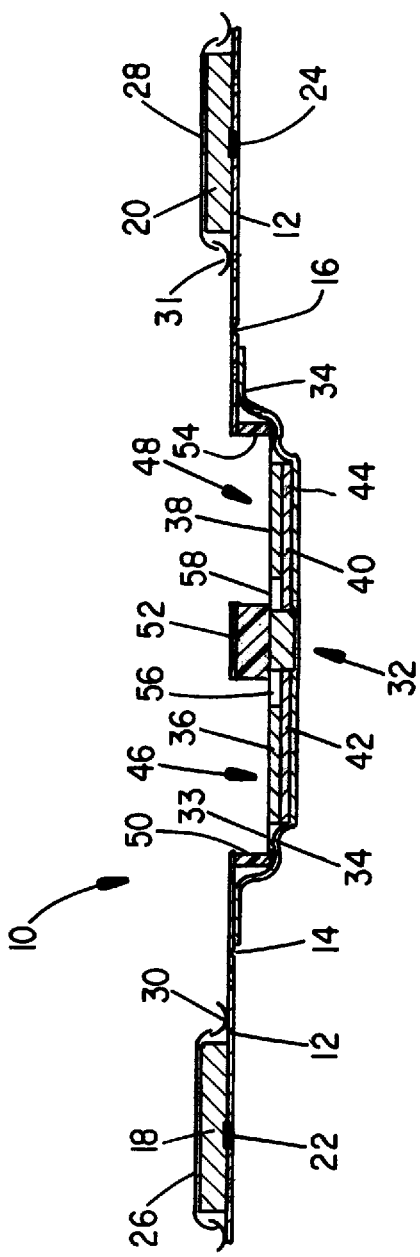
FIG. 1b is a schematic cross sectional view of the embodiment of FIG. 1a as assembled.
Figure 1D:
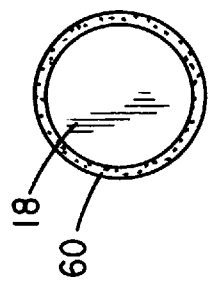
FIGS. 1c and 1d represent cross sectional and top views depicting an alternative embodiment of an anode or a cathode matrix.

Thus FIGS. 1a, 1b and 2 depict respectively an exploded view, a cross-sectional elevational view and a top view of one embodiment of such a device, generally at 10, as it is packaged and stored. The device 10 is stored as an elongated device designed to fold on itself when activated and used to form a compact skin-worn drug applicator. It includes a continuous backing or substrate layer 12 which is also designed as a release layer, as will be seen, provided with fold lines as at 14 and 16, respectively. An anode matrix 18 and cathode matrix 20 are respectively releasably adhered to the peel-away backing or continuous substrate layer 12 by rather smaller sized amounts of packaging adhesive release or transfer layers 22 and 24. The substrate layer 12 is generally a thin, water impermeable layer of a material such as polycarbonate, polyethylene, polypropolene or the like. Moisture impermeable covers 26 and 28 are in the nature of release coating layers that serve as protective barriers during storage of the anode matrix 18 and cathode matrix 20, respectively. The moisture impermeable covers 26, 28 include pull-tab devices as at 30 and 31 for easy peel-away removal at the time of device activation.

An iontophoretic circuit device, generally depicted by 32, is fixed to the opposite side of substrate 12 as by an adhesive-coated backing layer 34. The iontophoretic device 32 further includes an anode 36 and a cathode 38 electrically connected to an optional or selectively used electronic circuit depicted by 40 utilizing of electrically conductive layers 42 and 44, respectively.

The optional electronic circuit 40 is preferably of a known conventional type and includes a power source, resistors, switches and other conventional circuit components. These systems are well known to those skilled in the art as useful for controlling current flow and so need not be described here in greater detail. In the absence of the selective or optional electronic circuit 40, power for the device may be provided by spontaneous or galvanic means using oxidizing and reducing coatings, on the anode (for example, Zinc) and the cathode (for example, Silver Chloride).

The device as stored includes a pair of empty recesses or chambers 46 and 48 defined by portions of structural layers as at 50, 52 and 54 as best seen in the top view of FIG. 2, which are preferably made of pliable material such as a closed cell polyurethane foam, or the like. The empty chambers 46 and 48 are sized so as to receive cathode matrix 18 and anode matrix 20, respectively. Corresponding openings 46a and 48a are provided in the release layer 12. Fold lines 14 and 16 are located at the midpoint between the respective matrices 18 and 20 and chambers 46 and 48, respectively, and are positioned and angled such that the matrices are aligned to be received in the empty chambers when the substrate is folded during the activation sequence as will be described. Whereas the fold lines are depicted as a notch in the figures, those skilled in the art will recognize that there are many alternate ways to predetermine a line of preferential folding, such as using perforations, score lines, hinges, etc.

Figure 1C:
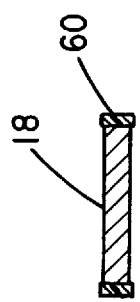

The bottoms of chambers 46 and 48 are provided with areas of transfer receiving adhesive layers at 56 and 58, respectively, which are designed to secure the matrices 18 and 20 to the electrodes 36 and 38, respectively of the iontophoretic device 32 as they are transferred from the packaging substrate 12 as the device is activated. FIG. 1c shows an exploded view of a matrix system for either an anode or cathode similar to that shown in FIG. 1a with the exception that a structural ring 60 is provided surrounding the matrix. The structural ring 60 is designed to transfer into the corresponding opening as at 46 in the activated device with the matrix 18.

FIGS. 3a–3e illustrate the steps in the activation process for the embodiment of the device depicted in FIGS. 1 and 2. In FIGS. 3a and 3b the pull-tabs 30, 31 have been utilized to remove the moisture impermeable membrane release liners or covers 26 and 28 from the matrices 18 and 20. As illustrated in FIGS. 3c and 3d, the substrates 12 and 13 are then folded respectively at fold lines 14 and 16 to engage the matrices 18 and 20 with the iontophoretic device 32. The matrices 18 and 20 are secured in place on the Iontophoretic device 32 by the adhesive at 56 and 58. This enables the substrate or backing layer 12 to be totally stripped away without disturbing the matrices 18, 20 which are also within openings 46a and 48a thereby exposing the adhered matrices so that the device can be turned over at FIG. 3e and applied to the skin of a patient utilizing the adhesive on the adhesive-coated backing layer 34, which also completes the circuit and thereby activates the device to initiate the transfer of the drug of interest.

FIG. 4 is a schematic cross-sectional view of an alternate configuration 62 of the device 10 of FIG. 1. In this embodiment, anode matrix 18 and cathode matrix 20 are contained in recessed portions 64 and 66 of substrate 12, respectively. Moisture impermeable release covers 26 and 28 are utilized as in the previous embodiment along with removing pull-tabs 30 and 31. This embodiment, however, eliminates the need for the adhesive layers 22 and 24 to maintain the matrices 18 and 20 in place prior to activation. This embodiment is particularly useful for situations in which the drug ions are not stable in the presence of adhesive material 22, 24.

FIG. 5 depicts another alternative embodiment in the form of a side-by-side arrangement at 70 in which the drug-containing matrices 18 and 20 are located on one side and the iontophoretic device is located on the other. A single fold line 72 separates the two and is all that is needed to transfer the matrices to the iontophoresis device for activation.

FIG. 6 depicts yet another embodiment 80, which is similar to the embodiment of FIG. 5 including a single fold line at 82, the only difference being the use of the single moisture impermeable release cover 84 with single corner pull-tab 86 to cover both matrices 18 and 20. This, of course, simplifies the activation process by accomplishing the peel-away removal of the matrix cover from both matrices in a single step.

Figure 7:
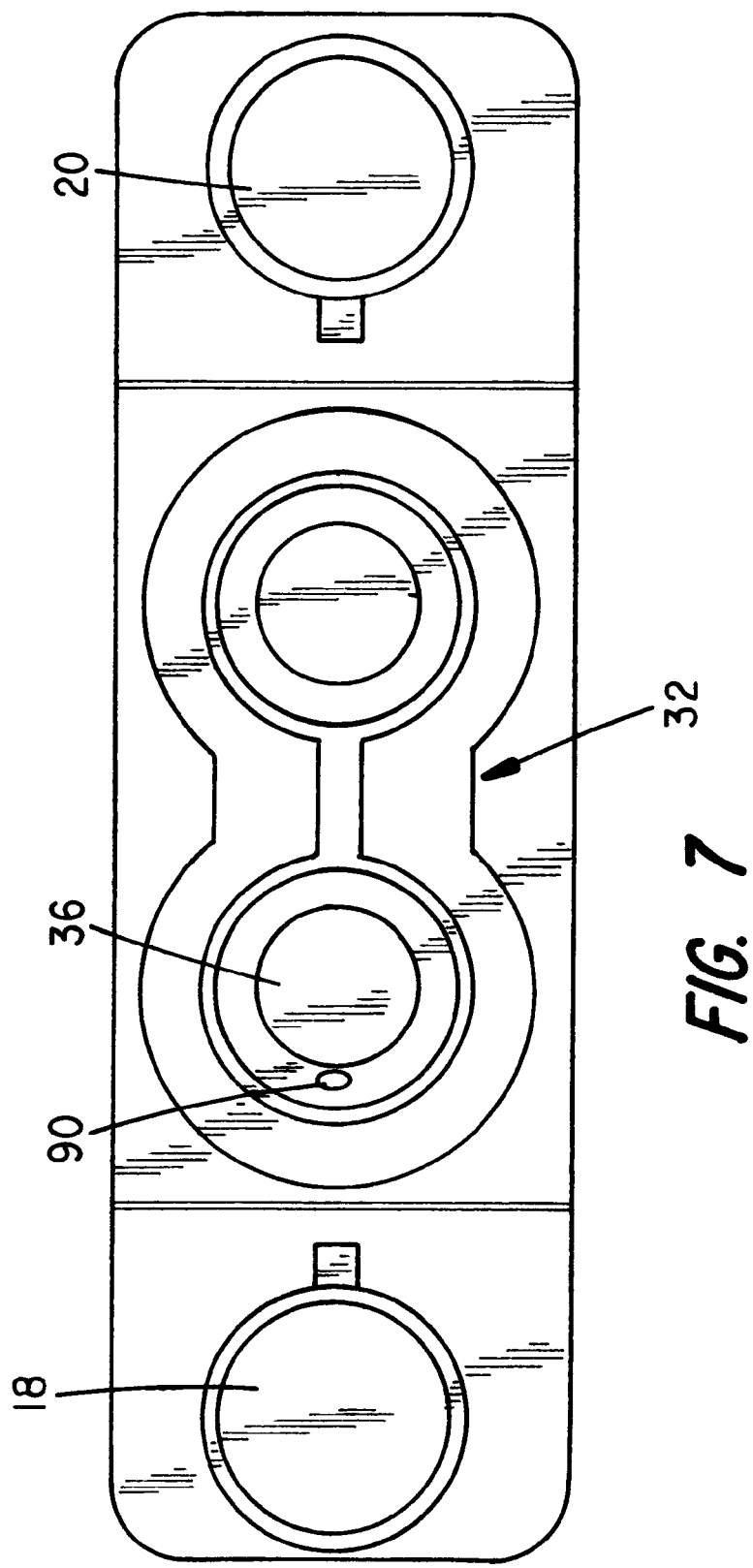
FIG. 7 is a top view of an alternate embodiment of the device of FIG. 1, in which the drug is stored in a dry state and dissolved at the time of activation.

FIG. 7 depicts a view similar to FIG. 2 of an embodiment that is similar to that depicted in FIGS. 1a, 1b and 2 but in which an additional drug layer depicted through opening 90 is incorporated into the iontophoretic delivery device 32 at the appropriate electrode 36. This configuration can be used in lieu of incorporating the drug in the matrix 18 as illustrated, or 20 as the case may be, when the drug is not stable over time in an aqueous matrix. The drug layer seen at 90 is in a dry state and may be incorporated into a filter pad or other suitable water soluble or insoluble matrix during storage. Upon activation, the drug layer at 90 is dissolved into either the anode gel matrix, as illustrated, or the cathode gel matrix 20, depending on the charge of the drug.

The aqueous matrices 18 and 20 in this invention are preferably formed of a hydrophilic gel material, to insure that the matrix maintains a uniform structure during the folding process. Obviously, if the matrix were in a low viscosity, e.g. liquid state, it would deform during the fold process. It has been found a 1–3% agarose, or 10–12% cross linked polyvinyl alcohol to be an acceptable examples of gel for this purpose. Substances which provide a high viscosity, such as polyvinylpyrrolidone, methyl cellulose, hydroxypropyl methylcellulose, carboxymethyl cellulose are also acceptable. Those skilled in the art will recognize the benefit of also incorporating additives such as humectants (ex guar gum) and anti-fungal agents (ex. methyl or butyl paraben). Further, it has been found beneficial to incorporate a fibrous material such as cellulose, polyester, or polypropylene into the matrix. This fibrous material serves several purposes; first, it serves to provide a defined shape for disperse of the aqueous solution during the manufacturing process. Second, it serves to help retain the shape of the matrix during the folding process. And third, it has been discovered that the fibrous material serves as a basis for proper adhesion. For example, an aqueous agarose hydrogel has been found to adhere very poorly to conventional medical adhesives, as found on for example medical tapes. However, the same gel solutions present in a fibrous matrix have been found to adhere very well.

One preferred use of the delivery system of this invention is for the delivery of the opioid compound fentanyl, as a means of managing pain due to, for example, the effects of chronic cancer. Fentanyl is a highly potent compound, and a very dangerous one in that, for example, too high of a dosage rate can lead to a respiratory depression. Transdermal delivery of fentanyl can be accomplished passively, when the drug is in the free base form, as the commercial product Duragesic (Johnson & Johnson). Fentanyl is iontophoreseable when formulated as an ionized hydrochloride or citrate salt, and is positively charged and therefore deliverable from the anode. An advantage of iontophoresis is derived from improved control opportunity; for example, a more rapid onset of action possible with iontophoresis as compared to passive introduction. Since the ionic form of fentanyl is not passively permeable through skin, theoretically, the rate and amount of fentanyl delivered can be regulated entirely by current flow. Iontophoretic devices for the delivery of fentanyl are described in U.S. Pat. Nos. 5,232,438, 6,171,294 and 6,216,033. In these devices, an activation switch initiates a pre-determined DC current flow (regulated by electronic circuitry) over a pre-determined timing (e.g. up to 20 minutes) interval to provide a bolus dose of fentanyl on the order of 60 micrograms.

It has been discovered according to the present invention that voltage regulation is a preferred and safer alternative to current regulation in the iontophoretic delivery of fentanyl. In current regulation, when the device is activated, an electronic circuit automatically adjusts an applied voltage to achieve a known current level. The necessary voltage is dependent on, among other things, the desired current level and patient skin resistance. Upon initiation of current, the skin is often dry, the applied voltage is therefore very high, and a high current density will be focused on an area of skin with the least amount of resistance. This concentration of current can itself cause skin damage to the local site, and lead to a compromise in skin integrity that can lead to passive transfer with otherwise non-passively transferable fentanyl ion. Therefore, control of total drug delivery is compromised in that it is no longer controlled by iontophoresis alone.

In voltage control, a fixed voltage is applied between electrodes, and the resulting current will vary in accordance to skin resistance (e.g. Ohms Law). It has been found that current will slowly increase over the course of time, as the skin hydrates under the electrodes and therefore becomes less resistive. Also, even though the process is slower, skin integrity is preserved in a preferred way for iontophoretic fentanyl delivery. With a voltage controlled circuit, current flow can be regulated in quasi fashion with incorporation of internal resistance to the fixed voltage source. In this way, the total system resistance is a function of skin resistance combined with internal circuit resistance. If the internal circuit resistance is high relative to skin resistance, the rate variability owing to patient-to-patient, site-to-site, and hydration rate differences are reduced. It has been discovered that voltage control in the range of 3–12 volts, with internal resistances in the range of 5–300 kohms are preferred, as they are adequate for rate control and for the preservation of skin integrity.

A significant disadvantage to passive delivery is derived from an inability to modulate delivery rate in a reversible fashion. This is a significant disadvantage in delivery of pain management drugs such as fentanyl, in that pain is generally not constant. In a current regulated iontophoretic system, the delivery rate is reversibly adjustable by raising or lowering an applied voltage to achieve a desired current level. However, this current regulating approach may lead to unacceptable skin damage, as described above. A simple two-level delivery rate, using a voltage regulating electronic circuit, has been discovered to be sufficient for pain management applications, where the level is adjusted by reversibly short circuiting a portion of the internal resistance.

Figure 8:
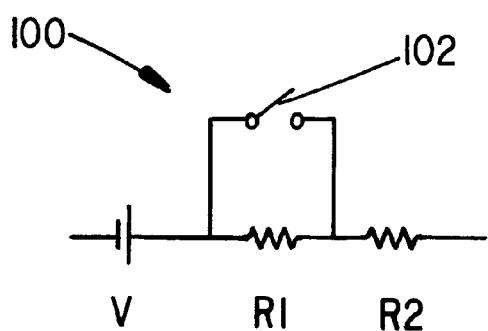
FIG. 8 is an electrical schematic of a preferred circuit for rate regulation.
Figure 9:
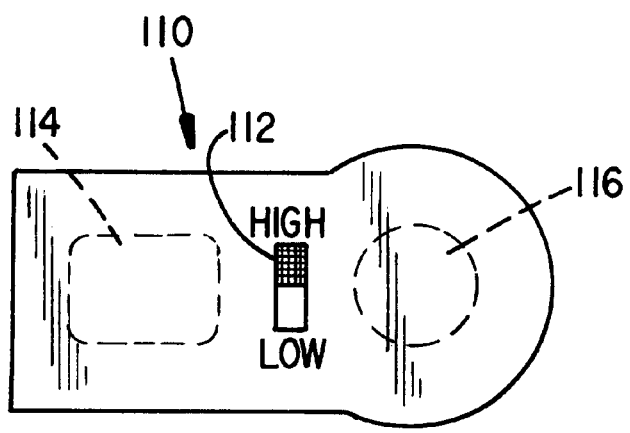
FIG. 9 is a top view of a two-position embodiment of the device of the invention suitable for the delivery system of fentanyl citrate as a means of pain management.

FIG. 8 is an electrical schematic of the preferred 2-level delivery rate regulating electronic circuit 100 having a patient adjustable switch 102 shown in the "low" position with both R1 and R2 in series in the circuit. FIG. 9 is a top view of an activated, fentanyl delivery device in accordance with the invention 110 with a patient adjustable two-position rate switch 112. Though they wouldn't be visible from the top, the electrodes are depicted with broken lines at 114 and 116 in FIG. 9. As shown, the device is in a "high" delivery rate status with a switch type connection engaged to reduce internal device resistance.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A self-contained, wearable, pre-packaged iontophoretic drug delivery system comprising:

(a) a removable substrate;

(b) an aqueous anode matrix removably carried on said substrate and isolated by a water impermeable release membrane;

(c) an aqueous cathode matrix removably carried on said substrate and isolated by a water impermeable release membrane;

(d) an iontophoresis device including an anode electrode and a cathode electrode and a source of electric power carried on said substrate;

(e) wherein said iontophoresis device includes shaped recesses associated with said anode and said cathode configured to receive said aqueous anode matrix and said aqueous cathode matrix, respectively, in conductive relation;

(f) at least one fold line on said removable substrate to enable the pre-packaged system to fold on itself to thereby associate said anode matrix and said cathode matrix with said anode electrode and said cathode electrode; and (g) an amount of a therapeutic ion species to be delivered transdermally by iontophoresis located in at least one of said anode matrix, said cathode matrix and said iontophoresis device.

2. An iontophoretic drug delivery system as in claim 1 further comprising an amount of adhesive to retain said aqueous anode matrix and said aqueous cathode matrix initially on said substrate.

3. An iontophoretic drug delivery system as in claim 1 wherein said water impermeable release membrane associated with said aqueous anode matrix is separate from said water impermeable release membrane associated with said aqueous cathode matrix and wherein both said water impermeable release membranes are provided with pull-tabs enabling them to be peeled off when desired.

4. An iontophoretic drug delivery system as in claim 1 wherein removal of said removable substrate exposes said anode matrix and said cathode matrix for application to the skin of a patient.

5. An iontophoretic drug delivery system as in claim 1 wherein said aqueous anode matrix and said aqueous cathode matrix are carried in recesses in said substrate.

6. An iontophoretic drug delivery system as in claim 1 wherein said substrate is provided with a plurality of fold lines.

7. An iontophoretic drug delivery system as in claim 1 wherein said therapeutic ion species is a form of fentanyl and is located in said anode matrix.

8. An iontophoretic drug delivery system as in claim 1 wherein said anode matrix and said cathode matrix include a hydrogel or highly viscous material.

9. An iontophoretic drug delivery system as in claim 8 wherein said hydrogel or highly viscous material is selected from the group consisting of agarose, polyvinyl alcohol, polyvinylpyrrolidone, methyl cellulose, hydroxypropyl methylcellulose and, carboxymethyl cellulose, and combinations thereof.

10. An iontophoretic drug delivery system as in claim 1 wherein said anode matrix and said cathode matrix include a fibrous material.

11. An iontophoretic drug delivery system as in claim 10 wherein said fibrous material is selected from the group consisting of cellulose, polyester and polypropylene and combinations thereof.

12. An iontophoretic drug delivery system as in claim 10 wherein said anode matrix and said cathode matrix include a hydrogel or highly viscous material.

13. An iontophoretic drug delivery system as in claim 11 wherein said anode matrix and said cathode matrix contain a hydrogel material or highly viscous material selected from the group consisting of agarose, polyvinyl alcohol, polyvinylpyrrolidone, methyl cellulose, hydroxypropyl methylcellulose, carboxymethyl cellulose are also acceptable.

14. An iontophoretic drug delivery system as in claim 1 wherein said amount of therapeutic ion species to be delivered transdermally by iontophoresis is located in said iontophoresis device in a dry state prior to activation.

15. An iontophoretic drug delivery system as in claim 1 wherein said anode matrix and said cathode matrix include at least one additive selected from the group consisting of humectants and antifungel agents.

16. An iontophoretic drug delivery system as in claim 1 wherein said iontophoresis device includes a voltage control system.

17. An iontophoretic drug delivery system as in claim 16 wherein said voltage control device further includes a two-position, high-low switch.

* * * * *